US006548295B2

(12) United States Patent
André et al.

(10) Patent No.: US 6,548,295 B2
(45) Date of Patent: Apr. 15, 2003

(54) COMPLEX OF LIPO-VIRO-PARTICLES, METHOD OF PREPARATION AND APPLICATIONS

(75) Inventors: Patrice André, Lyons (FR); Vincent Lotteau, Vourles (FR); Glaucia Paranhos-Baccala, Lyons (FR); Florence Komurian-Pradel, Poleymieux (FR)

(73) Assignees: Bio Merieux, Mercy l'Etoile (FR); Institut National de la Sante et de Recherche Medicale, Paris (FR)

( * ) Notice: Subject to any disclaimer, the term of this patent is extended or adjusted under 35 U.S.C. 154(b) by 0 days.

(21) Appl. No.: 09/917,915

(22) Filed: Jul. 31, 2001

(65) Prior Publication Data

US 2002/0058044 A1 May 16, 2002

(30) Foreign Application Priority Data

Jul. 31, 2000 (FR) .............................. 00 10085

(51) Int. Cl.[7] .............................. C12N 5/00; C12Q 1/70; C12Q 1/68; G01N 33/53; A61B 5/055
(52) U.S. Cl. .............................. 435/325; 435/6; 435/39; 435/7.1; 435/5; 424/9.34
(58) Field of Search .................. 435/5, 6, 39, 7.1, 435/325; 424/9.34

(56) References Cited

U.S. PATENT DOCUMENTS

| 5,679,342 A | 10/1997 | Houghton et al. | ........ 424/93.21 |
| 5,766,919 A | 6/1998 | Yoshikura et al. | ........ 435/235.1 |

OTHER PUBLICATIONS

"Density Hetrogeneites Of Hepatitis C Virus In Human Sera To The Binding Of β–Lipoproteins And Immunoglubulins" by R. Thomssen et al., Medical Microbiology and Immunology (1993) 182, pp. 329–334.

"Establishment Of Persistent Hepatitis C Virus Infection And Replication in Vitro" by Stefanie Seipp et al., Journal of General Virology (1997), 78 pp. 2467–2476.

"Equilibrium Centrifugation Studies Of Hepatitis C Virus: Evidence For Circulating Immune Complexes" by Minako Hijikata et al., Journal of Virology, Apr. 1993, pp. 1953–1958.

"Isolation Of A cDNA Clone Derived From A Blood–Borne Non–A, Non–B Viral Hepatitis Genome" by Qui–Lim Choo et al., Science vol. 244, Apr. 21, 1989, pp. 359–361.

"Cultivation Of Hepatitis C Virus In Primary Hepatocyte Culture From Patients With Chronic Hepatitis C Results In Release Of High Titre Infectious Virus" by T. Ito et al., Journal fo General Virology(1996), 77, 1043–1054.

(List continued on next page.)

Primary Examiner—Hankyel T. Park
(74) Attorney, Agent, or Firm—Oliff & Berridge, PLC

(57) ABSTRACT

The complex consists of LVPs associated with human immunoglobulins having a density of less than 1.063 g/ml.

It may be obtained by a method according to which a plasma or serum sample taken from a patient infected with HCV is made available, the LVPs are separated from the said sample by centrifugation according to their density, and the LVPs associated with human immunoglobulins are separated using protein A, anti-human immunoglobulins or any other molecule capable of binding human immunoglobulins.

27 Claims, 2 Drawing Sheets

OTHER PUBLICATIONS

"Continuous Cultures Of Fused cells Secreting Antibody Of Predefined Specifity" by G. Kohler et al.; Nature, vol. 256, Aug. 7, 1975, pp. 495–497.

"Antibodies To Major Histocompatibility Antigens Produced By Hybrid Cell Lines" by G. Galfre et al., Nature, vol. 266, Apr. 7, 1977, pp. 550–552.

"Production Of A High–Titer Antibody To Bile Acids" by A. Roda et al., Journal of Steroid Biochemistry, vol. 13, pp. 449–454.

"Anti–CD3εF(ab')$_2$ Fragments Inhibit T Cell Expansion In Viro During Graft–Versus–Host Disease Or The Primary Immune Response To Nominal Antigen [1,2]" by Bruce R. Blazar et al., The American Association of Immunologists, 1997, pp. 5821–5833.

"Single–Chain Antigen–Binding Proteins" by Robert E. Bird et al., Science, vol. 242, Oct. 21, 1988, pp. 423–426.

"Cloning And Sequencing Of The $V_h$ and $V_k$ Genes Of An Anti–CD2 Monoclonal Antibody, And Construction Of A Mouse/Human Chimeric Antibody" by J. Biochem. vol 120, No. 3, 1996, pp. 657–662.

"A Recombinant Immunotoxin Consisting Of Two Antibody Variable Domain Fused To Pseudomonas Exotoxin" by Vijay K. Chaudhary et al.; Nature, vol. 339, Jun. 1, 1989; pp. 394–397.

"Cleavage Of Structural Proteins During The Assembly Of The Head Of Bacteriophage T4" by U.K. Laemmli; Nature. vol. 227, Aug. 15, 1970, pp. 680–685.

"Electrophoretic Transfer of Proteins From Polycrylamide Gels To Nitrocellose Sheets: Procedure And Some Applications" by Harry Towbin et al.; Proc. Natl. Acad Sci. USA, vol. 76, No. 9, Sep. 1979, pp. 4350–4354.

"The LightCycler™:: A Microvolume Multisample Fluroimeter With Rapid Temperature Control" by C.T. Wittwer et al., BioTechniques, vol. 22., No. 1 (1997), pp. 176–181.

COMPLEX OF LIPO-VIRO-PARTICLES, METHOD OF PREPARATION AND APPLICATIONS

BACKGROUND OF THE INVENTION

Hepatitis C is the main cause of hepatitis acquired by transfusion. Hepatitis C may also be transmitted by other percutaneous routes, for example by intravenous drug injection. The risk of contamination of health professionals is moreover not negligible.

Hepatitis C is distinguishable from other forms of liver diseases associated with viruses, such as hepatitis A, B or D. Hepatitis C virus (HCV) infections are often chronic with, as a consequence, liver diseases such as hepatitis, cirrhosis and carcinoma in a large number of cases.

Although the risk of transmission of the virus through transfusion has diminished because of the selection of blood donors, the frequency of hepatitis C remains high. Currently, about 170 million people worldwide are chronically infected with HCV. Populations at high risk are found mainly in recipients of blood transfusions and intravenous drug users, but asymptomatic blood donors exist who do not belong to these high-risk groups and in whom circulating anti-HCV antibodies have been found. For the latter, the route of infection has not yet been identified.

HCV was the first hepatotropic virus isolated by means of molecular biology techniques. The sequences of the viral genome were cloned before the viral particle was visualized.

HCV is a 9.5 kb, positive single-stranded RNA virus which replicates via a complementary RNA copy and whose translational product is a precursor of a single polyprotein of about 3000 amino acids. The 5' end of the HCV genome corresponds to an untranslated region adjacent to the genes which encode the structural proteins, the core protein of the nucleocapsid and the two envelope glycoproteins, E1 and E2/NS1. The untranslated 5' region and the core gene are relatively well conserved in the various genotypes, but the E2 envelope proteins are encoded by a hypervariable region which is different from one isolate to another. The 3' end of the HCV genome contains the genes which encode the nonstructural (NS) proteins and a well conserved noncoding 3' region.

Because of its genomic organization and its presumed mode of replication, HCV has been classified in a novel genus of the Flaviviridae family, the Hepaciviruses.

Numerous techniques have been developed for the diagnosis of an HCV infection. For example, diagnostic immunological assays have been carried out to detect antibodies directed against HCV proteins in the sera of patients. The synthesis of cDNA by reverse transcription of the viral RNA and PCR amplification have also been used to detect the HCV genome, as the indirect measurement of a potentially infectious virus in the sera of chronically infected humans or those of experimentally infected chimpanzees. Moreover, on the basis of gene cloning, hybridization techniques with a DNA probe have also been developed.

However, it is recognized that existing diagnostic techniques lack sensitivity and/or specificity and/or suffer from implementation difficulties. By way of example, with the method of hybridization of probes, it is impossible to distinguish between a virus with low infectivity and a virus with high infectivity. It is therefore necessary, but difficult to carry out, to inoculate the virus which has to be tested into a chimpanzee and to test the resulting infection on the animal.

It is therefore of primary importance, from the point of view of public health, to be able to develop specific, sensitive and practical methods for identifying and screening HCV carriers. One of the solutions could be to produce a very efficient in vitro system for culturing HCV which would make it possible to obtain propagation of the virus, in particular to study its mechanisms of replication, to test neutralizing antibodies or antiviral agents, as well as to develop biological materials, diagnostic trials and vaccine preparations. Indeed, although the complete HCV sequence has been available since 1989 (Q. L Choo et al., Science 244, 359 (1989)), understanding of the life cycle and the mode of replication of HCV has been hampered by a lack of an appropriate in vitro culture system. Ito et al. (J. Gen, Virol. 77: 1043–1054 (1996)) have indeed confirmed maintenance of the replication of HCV in primary cultures of human hepatocytes obtained from patients carrying HCV and for whom the disease was chronically established, and suggested a passage of infection, but problems relating to the propagation of the virus remain (impossibility of long term culture) and the system developed is limited by the need for a supply of human liver and the cumbersome nature of the technique. Moreover, up until now, there is no general consensus on the tropism of HCV and all the cellular receptors for the virus have not yet been identified.

Viral RNA-containing particles which are very heterogeneous in density are present in the plasma of patients infected with HCV. This heterogeneity in the density of the particles containing viral RNA is attributed to their association in variable proportion with lipoproteins (Thomsen et al., 1993, Med. Microbiol. Immunol. 182: 639). In the description of the present patent application, the inventors have called these hybrid particles LVPs (lipo-viro-particles). The distribution of each of these forms along a density gradient varies from one patient to another. The existing analyses of particles of low density show densities covering those of the LDLs (Low Density Lipoproteins) and of the VLDLs (Very Low Density Lipoproteins). The size described (50 nm) bring them close to the VLDLs.

The nature of the abovementioned LVPs containing viral RNA is up until now not precisely known, but the present inventors have shown for the first time that the LVPs are associated with human immunoglobulins and that it is in these fractions of LVPs, whose density is equal to or less than 1.063 g/ml, associated with human immunoglobulins, that the HCV virus RNA is predominantly present, contrary to the known data (Hijikata et al., J. Virol. (1993), 1953–1958). Indeed, Hijikata et al. have shown that there were no human immunoglobulins in the particles having a density of less than 1.06 g/ml, and that it is in the particles of this density that a high infectivity is found in chimpanzees. These experimental data could constitute at least one basis of explanation of the chronicity of the disease, which has not yet been elucidated up until now, and furthermore open perspectives for novel methods of in vitro culture of the HCV virus.

SUMMARY OF THE INVENTION

Accordingly, the subject of the present invention is a complex consisting of LVPs associated with human immunoglobulins, the said complex having a density of less than 1.063 g/ml and preferably between 1.0063 and 1.063 g/ml, as demonstrated by centrifugation, for example on a sodium bromide gradient.

BRIEF DESCRIPTION OF THE DRAWINGS

The present invention is now described with reference to the attached drawings, in which.

DETAILED DESCRIPTION OF THE INVENTION

Figure 1:
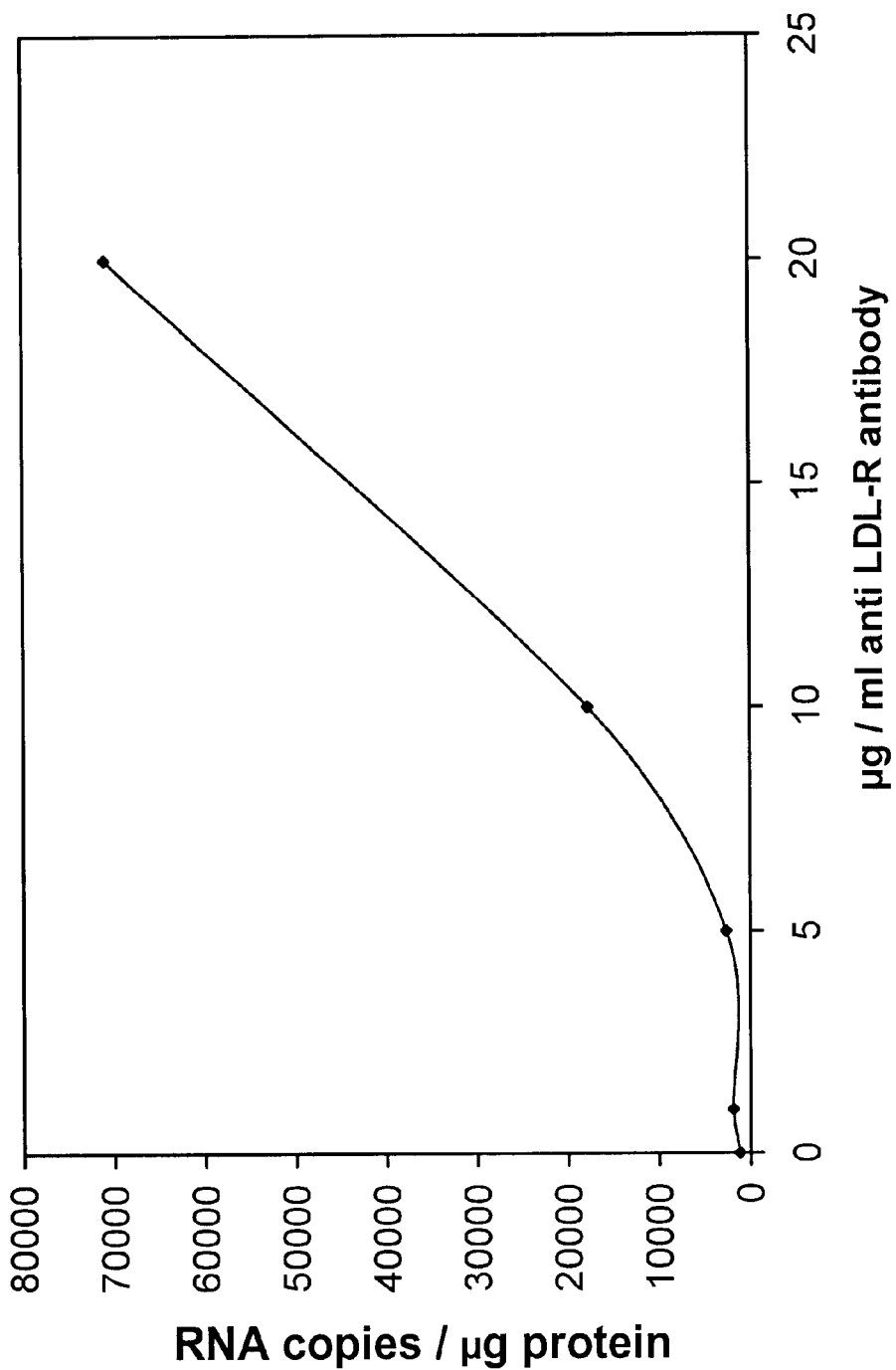
FIG. 1 shows the quantity of lipo-vivo particles (LVPs) associated with immunoglobulins (Ig) (i.e. LVP/Ig+) internalized as determined by the quantification of viral RNA.

The invention also relates to a method for preparing the said LVPs associated with human immunoglobulins (LVP/Ig) complex which consists in carrying out a separation by gradient centrifugation from a plasma or serum sample from a patient for the production of a fraction of the LVP/Ig complex having a density of less than 1.063 g/ml and preferably of between 1.0063 and 1.063 g/ml, and then a purification of the fraction of the said complex by protein A or human anti-immunoglobulins or by any other molecule capable of binding human immunoglobulins (coupled to a support, such as beads or sepharose). This method makes it possible "to enrich" the initial sample with LVP/Ig complex while eliminating the lipoproteins not belonging to the LVP/Ig complex.

The LVP/Ig complex obtained, preferably purified according to the mode of preparation of the invention can be used for carrying out a method for the in vitro culture of the HCV virus. Indeed, a large number of cells possess, at their surface, a receptor for the Fc fragment of the immunoglobulins and it is thus possible to cause the viral RNA associated with the immunoglobulins to penetrate into these permissive cells, via the interaction between the Fc fragment of the immunoglobulins and one of its membrane receptors, and to bring about the propagation and the replication of the HCV virus in vitro.

Accordingly, the subject of the present invention is also a method for the in vitro culture of the HCV virus, according to which the LVP/Ig complex (preferably purified according to the method of the invention) and permissive cells which contain at their surface at least one type of receptor for the Fc fragment of the immunoglobulins or permissive cells expressing at least one receptor for a molecule having the capacity to bind the immunoglobulins are brought into contact, in a given medium and under appropriate conditions, the said permissive cells being capable of allowing the propagation and the replication of the HCV virus in vitro. Of course, the expression of this or these receptors may be either spontaneous or induced, in particular by transfection.

Among the permissive cells expressing at least one type of receptor for the Fc fragment of the immunoglobulins, there may be mentioned by way of nonlimiting examples mononuclear cells (stem cells derived from the bone marrow, monoblasts, promonocytes, monocytes and macrophages) macrophage precursor cells, B lymphocytes, NK cells, hepatocytes, dendritic cells, epithelial cells, vascular endothelium cells, mastocytes, Langerhans' cells; syncytiotrophoblasts, eosinophilic, basophilic and neutrophilic polynuclear cells, platelets.

Among the permissive cells expressing at least one receptor for a molecule having the capacity to bind immunoglobulins, there may be mentioned erythrocytes and their precursors, macrophages, monocytes, polymorphonuclear leukocytes (eosinophilic, basophilic and neutrophilic polynuclear cells), B lymphocytes and dendritic cells.

The macrophages are preferably chosen from the group which consists of histiocytes, alveolar macrophages, macrophages of the spleen and of the lymphoid tissue, Kuppfer cells, osteoclasts, type A synovial cells, tissue macrophages and precursor cells from which these cells are derived. Because the HCV virus is hepatotropic, the cells of human or animal primary hepatocytes, the cells of the group of human or animal hepatocarcinoma cell lines and the Kuppfer cells are advantageously preferred. However, since it has been shown that HCV is capable of being propagated and of replicating in the lymphocytes, the B lymphocytes are also preferred permissive cells.

When the permissive cells are cells of human or animal primary hepatocytes, cells of the group of human or animal hepatocarcinoma cell lines or Kuppfer cells, the infection of the said cells by the HCV virus is carried out via the interaction between the Fc fragment of the human immunoglobulins and at least one of the receptors for the Fc fragment present at the surface of the said permissive cells but also via the interaction of the LVPs which are ligands for a route of endocytosis associated with the receptors for the lipoproteins, such as the LDL-receptor and the LSR-receptor which are present at the surface of these same permissive cells.

The term HCV virus refers to any viral species, among which the strains which are pathogenic for humans, the attenuated strains and the defective strains derived from the said strains. Indeed, it is known that the RNA viruses exhibit a high rate of spontaneous mutations. Multiple strains may therefore exist which may be virulent to a greater or lesser degree. It is within the capability of persons skilled in the art to identify such strains, for example by nucleic and/or peptide sequence homology relative to a reference strain and/or by identifying a strain or an isolate with respect to morphological and/or immunological criteria.

The term "in vitro" cellular system refers to cells which have been replicated in vitro and therefore includes the primary cultures, the cultures derived from primary cultures, the primary lines and the lines derived from the said primary lines. Because it is known that induced or spontaneous modifications may occur in the karyotype during storage or transfer, the cells derived from a reference cell line may not be strictly identical to the original cells or cultures and the invention includes such variants.

The term cell line refers to the established, immortalized or spontaneous lines. In practice, to carry out a viral culture of interest, it is necessary for the virus to be able to propagate in vitro in a culture in which the cells are capable of multiplying permanently and thus allow the viral propagation. The cell line is therefore preferably an established cell line or a cell line which results from immortalization by various methods. This may be carried out (i) by the establishment of a stable, established or continuous line or by coculturing permissive cells with tumorized permissive cells of the same nature, which are capable of multiplying indefinitely and of allowing the propagation of the virus within the culture, the viral inoculation taking place within the culture (ii) using primary cells infected with the virus which are then cocultured with permissive tumorized cells which allow the propagation of the virus within the culture of the cell line thus established or (iii) by viral infection of a cell line, for example an immortalized line of B lymphocytes, for example by the Epstein-Barr virus.

The appropriate medium selected for the HCV culture is the RPMI medium or a medium derived from the RPMI medium. Preferably, it is the RPMI 1640 medium supplemented with:

penicillin 1%
streptomycin 1% glutamine 2 mM decomplementized FCS (foetal calf serum) 10%.

Optionally, for the culture of certain permissive cells, the abovementioned medium comprises, furthermore, 50 µM beta-mercaptoethanol.

Several passages of permissive cells thus infected are carried out and the presence of the said virus is detected in the infected permissive cells and in the culture supernatant by RT-PCR and/or by an immunological technique, such as by indirect immunofluorescence using an antibody specific for the said virus and/or by flow cytometry.

The method of the invention, which makes it possible to obtain propagation of the HCV virus, is useful in particular for studying its replication mechanism, for testing neutralizing antibodies and antiviral agents, and for developing biological materials for diagnosis and therapy. Moreover, the method of the invention makes it possible to obtain an infected cell line useful for screening and/or selecting at least one antiviral molecule, by bringing the infected cell line and the antiviral molecule into contact.

The invention also relates to a method for preparing a composition for the detection, in a sample, of antibodies directed against HCV which comprises at least a partial or complete purification of the viral particles of the said virus or of the polypeptides obtained from the method of the invention. The expression partial or complete purification is understood to mean, for example, a purification by ultracentrifugation on a sucrose gradient, by differential precipitation in ammonium sulphate, a gel chromatography or any other method well known to persons skilled in the art. In particular, the said viral particles or the said polypeptides are attached to a solid support.

Moreover, the invention relates to a method for producing antibodies or fragments of antibodies directed against the HCV virus according to which an animal is immunized with the complex consisting of LVPs associated with human immunoglobulins having a density of less than 1.063 g/ml, preferably of between 1.0063 and 1.063 g/ml or with fractions of the said complex; the said complex being optionally prepared according to the method described above. The complex may thus be subjected to a step of treatment prior to the immunization, for example by treating with detergents or chaotropic agents, for the production of fractions consisting of viral proteins, lipids and phospholipids. The production of polyclonal and monoclonal antibodies or fragments of antibodies forms part of the general knowledge of persons skilled in the art. There may be mentioned, by way of example, Köhler G. and Milstein C. (1975) Continuous culture of fused cells secreting antibody of predefined specificity, Nature, 256: 495–497 and Galfre G. et al. (1977) Nature, 266: 522–550 for the production of polyclonal antibodies and Roda A., Bolelli G. F. Production of high titer antibody to bile acids, Journal os Steroid Biochemistry, Vol. 13, pp 449–454 (1980) for the production of polyclonal antibodies. The antibodies are produced by immunizing mice or rabbits with the LVP/Ig+ complex or with fractions of the said complex comprising viral proteins, lipids and phospholipids. The animals are subjected to an injection of immunogen using complete Freund's adjuvant. The sera and the hybridome culture supernatants obtained from the immunized animals are analyzed for their specificity and their selectivity using conventional techniques, such as for example ELISA or Western blot tests. The hybridomes producing the most specific and the most sensitive antibodies are selected. Monoclonal antibodies may also be produced in vitro by cell culture of the hybridomes produced or by recovering ascitic fluid, after intraperitoneal injection of the hybridomes into mice. Regardless of the mode of production, as supernatant or as ascites, the antibodies are then purified. The methods of purification used are essentially filtration on ion-exchange gel and exclusion chromatography or immunoprecipitation. A sufficient number of antibodies are screened in function tests to identify the most efficient antibodies. The in vitro production of antibodies, of fragments of antibodies or of derivatives of antibodies, such as chimeric antibodies produced by genetic engineering is well known to persons skilled in the art.

More particularly, the expression fragment of antibodies is understood to mean the F(ab)2, Fab, Fab', sFv (Blazar et al., 1997, Journal of Immunology 159: 5821–5833 and Bird et al., 1988, Science 242: 423–426) fragments of a native antibody and the expression derivative is understood to mean, inter alia, a chimeric derivative of a native antibody (see for example Arakawa et al., 1996, J. Biochem 120: 657–662 and Chaudray et al., 1989, Nature 339: 394–397).

The invention also relates to a method for the in vitro culture of the HCV virus according to which a complex consisting of LVPs associated with human immunoglobulins (LVP/Ig) as defined above is made available, the said complex is brought into contact with protein A for the production of an LVP/Ig/protein A complex, the said LVP/Ig/protein A complex is brought into contact with at least one antibody specific for at least one cell receptor for the production of an LVP/Ig/protein A/antibody complex and the said LVP/Ig/protein A/antibody complex and permissive cells which contain or express at their surface at least one cell receptor having the capacity to bind the antibody are brought into contact, in a culture medium and under appropriate conditions; the said permissive cells being capable of allowing the propagation and the replication of the HCV virus in vitro. According to this method and preferably:

- protein A is coupled to a support, such as beads or sepharose,
- the antibody is antibody specific for at least one of the receptors for the LDLs and the permissive cells contain or express at their surface at least one receptor for the LDLs,
- the permissive cells are chosen from human or animal primary hepatocytes and the cells of the group of human or animal hepatocarcinoma cell lines, such as the cells of the human heptacarcinoma line HepG2,
- the culture medium is the DMEM medium supplemented with 10% FCS,
- the presence of the HCV virus in the permissive cells is detected by RT-PCR and/or by immunological technique, such as by indirect immunofluorescence, in particular using an antibody specific for the said virus and/or by flow cytometry.

In the method of the invention, protein A is added in excess, which means that the protein A which is not bound to the human immunoglobulins of the LVP/Ig is still available, adsorbed to the surface of the LVPs, to bind to the antibody specific for a given cell receptor. Of course, the antibody may be a polyclonal or monoclonal antibody, but preferably will be a monoclonal antibody to ensure better specificity.

The invention also relates to a method for preparing a composition for the detection, in a sample, of antibodies directed against the HCV virus which comprises at least a partial or complete purification of the HCV viral particles or of the polypeptides obtained from a method of culture as defined above. Preferably for the preparation of the said composition, the viral particles or the polypeptides are attached to a solid support.

The subject of the invention is also a method for charging in vitro antigen presenting cells (APCs), according to which a complex consisting of LVPs associated with human immunoglobulins (LVP/Ig) as defined in either of claims 1 and 2 is made available, the said complex is brought into contact with protein A for the production of an LVP/Ig/protein A complex, the said LVP/Ig/protein A complex is brought into contact with at least one antibody specific for at least one cell receptor of the antigen presenting cells (APCs) collected from a human being or an animal for the production of an LVP/Ig/protein A/antibody complex and the said LVP/Ig/protein A/specific antibody complex is brought into contact with the said antigen presenting cells. The APCs are involved in the process of preparing the exogenous antigens to produce immunogenic peptides which bind to the molecules of the Major Histocompatibility Complex class I or II allowing the stimulation of the lymphocytes. The term APCs generally covers the macrophages, the B cells and the dendritic cells. In the present invention, there is particular focus on the dendritic cells, but this is not at all limiting and the method covers any antibody which is capable of binding to at least one receptor of the APCs. When the antigen presenting cells are dendritic cells, the antibody is an antibody specific for at least one cell receptor of the dendritic cells which is chosen from the "scavenger" receptors A and B, the mannose receptor and the "Toll Like Receptors" (TLRs). In the method of charging of the invention, the APCs are autologous, which means that they are collected from a human being or an animal and that after charging in vitro according to the method of the invention they are reintroduced into the same human being or animal to induce a humoral and cellular response. Reference is generally made to cell therapy.

The invention also relates to the charged APCs which can be obtained according to the method described above and to a therapeutic composition intended to induce a humoral and cellular response in a human being or an animal comprising a therapeutic agent which consists of antigen presenting cells charged according to the method of the invention. Furthermore, the invention also covers the antigen presenting vesicles or "exosomes" which are capable of being obtained from the APCs. The said composition comprises the usual adjuvants and/or diluents and/or excipients for the preparation of a therapeutic or prophylactic composition for the treatment or prophylaxis of immunological disorders or infections, provided that they are pharmaceutically acceptable.

The definitions of the pharmaceutically acceptable excipients, diluents and adjuvants are given in Remington's Pharmaceutical Sciences 16th ed., Mack Publishing Co.

Thus according to the invention, the method for the treatment or prophylaxis of an HCV virus infection consists in administering to a human being or to an animal, at predetermined doses, a therapeutic composition as defined above.

The invention also relates to a method for the production of antibodies or fragments of antibodies directed against the HCV virus, according to which an animal is immunized with an LVP/Ig/protein A/antibody complex which can be obtained by a method according to which, a complex consisting of LVPs associated with human immunoglobulins (LVP/Ig) as defined above is made available, the said complex is brought into contact with protein A for the production of an LVP/Ig/protein A complex, the said LVP/Ig/protein A complex is brought into contact with at least one antibody specific for at least one cell receptor of antigen presenting cells (APCs) for the production of an LVP/Ig/protein A/antibody complex. Preferably, the antigen presenting cells are dendritic cells and the antibody is an antibody specific for at least one cell receptor of the dendritic cells chosen from the "scavenger" receptors A and B, the mannose receptor and the "Toll Like Receptors" (TLRs)

FIG. 1 represents the quantity of LVP/Ig+ internalized, determined by quantification of the viral RNA. On the x-axis are represented the quantities in µg/ml of anti-LDL receptor antibodies and on the y-axis is represented the number of copies of RNA per µg of protein A.

Figure 2:
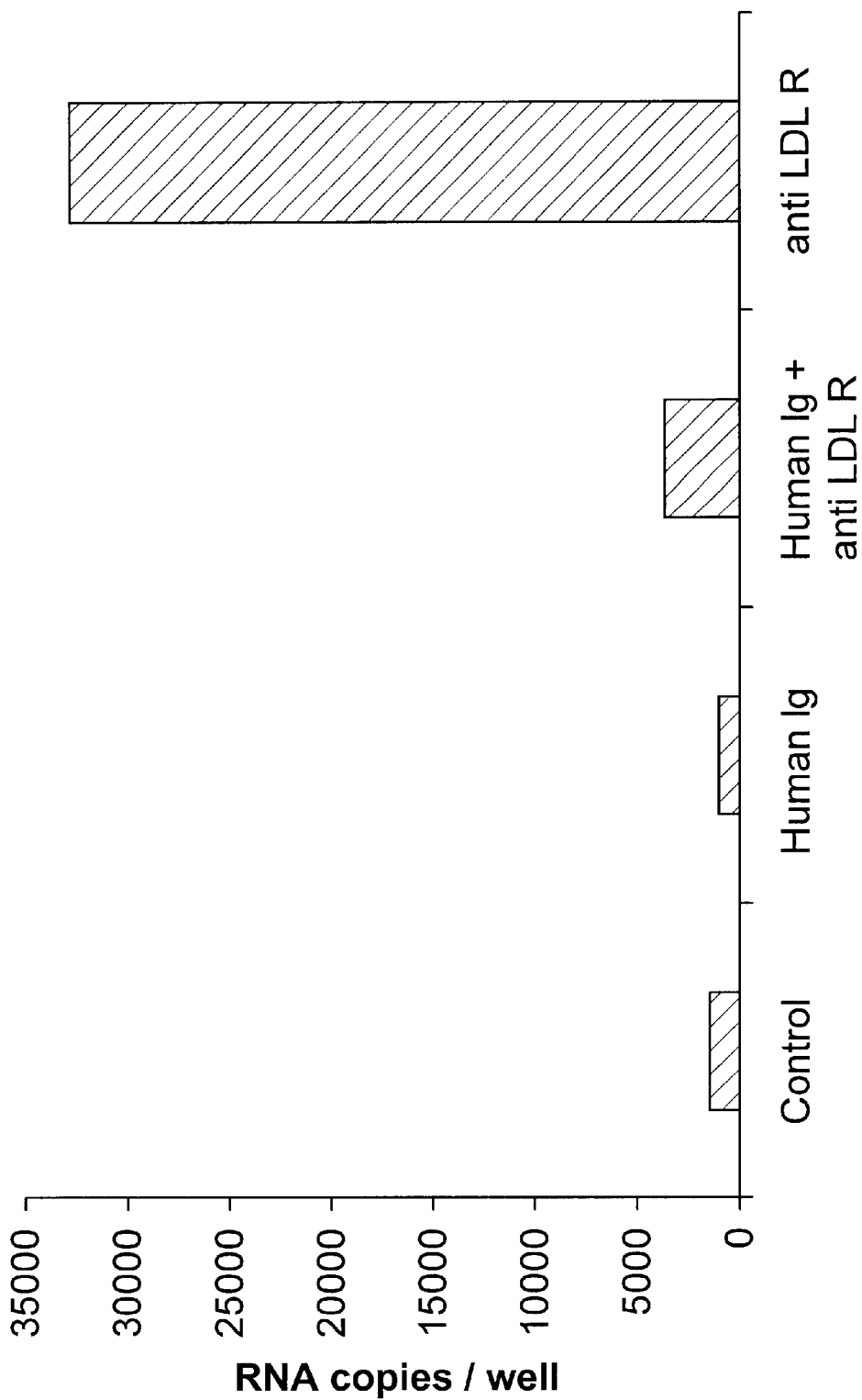
FIG. 2 shows the copy number of viral RNA obtained under various assay conditions.

FIG. 2 represents the copy number of viral RNA obtained per well in the presence of human immunoglobulins, of human immunoglobulins and anti-LDL receptor antibodies, of anti-LDL receptor antibodies and the control.

EXAMPLES

Example 1

Preparation of the Biological Material

The separation of the lipoproteins is carried out on plasma or serum from a patient who has fasted for 12 hours and detected positive for the hepatitis C virus.

1% of an EDTA solution (0.15 M NaCl-0.1 M EDTA) is added to the blood collected from the patient. The mixture is centrifuged for 10 minutes at 3500 rpm, at the temperature of 4° C. The plasma is then harvested and stored at 4° C. until it is used.

The blood from the patient is harvested over a dry tube and, after clotting, centrifuged for 10 minutes at 3000 rpm, at the temperature of 4° C. The serum is collected and stored at 4° C. until it is used.

(i) Production of a fraction comprising LVPs having a density of less than 1.0063 g/ml, of a fraction comprising LVPs having a density of between 1.0063 g/ml and 1.063 g/ml, and of a fraction comprising LVPs greater than 1.063 g/ml.

The plasma and the serum are respectively ultracentrifuged for 4 hours at 100,000 rpm, at 4° C. in a TL100 apparatus marketed by the company Beckman and comprising a TL100.4 rotor. The top fraction which contains the LVPs having a density of less than 1.0063 g/ml is recovered and stored at 4° C. The bottom fraction is adjusted to a density of 1.063 g/ml by addition of 7.21 g of NaBr per 100 ml of the fraction. The bottom fraction is then ultracentrifuged for 4 hours at 100,000 rpm, at 4° C., in a TL100 apparatus comprising a TL100.4 rotor. The resulting top fraction containing the fraction having a density of between 1.0063 g/ml and 1.063 g/ml is recovered and stored at 4° C.

(ii) Production of a fraction comprising LVPs having a density of less than 1.025 g/ml, of a fraction comprising LVPs having a density of between 1.025 g/ml and 1.063 g/ml, and of a fraction comprising LVPs having a density of greater than 1.063 g/ml.

The plasma and the serum are respectively adjusted to a final density of 1.025 g/ml by addition of 2.518 g of NaBr per 100 ml. A centrifugation is carried out for 4 hours at 100,000 rpm, at 4° C. on the TL100 apparatus comprising a TL100.4 rotor.

The top fraction which contains the fraction having a density of less than 1.025 g/ml is recovered and stored at 4° C. The bottom fraction is adjusted to a density of 1.063 g/ml by addition of 4.84 g of NaBr per 100 ml. The bottom fraction is then ultracentrifuged for 4 hours at 100,000 rpm, at 40° C., in the TL100 apparatus comprising a TL100.4 rotor. The resulting top fraction containing the LDLs is recovered and stored at 4° C.

The various fractions harvested are then dialysed for 18 hours at 4° C. against the 0.15 M NaCl/0.24 mM EDTA buffer. The fractions are then recovered and filtered on a 0.45µ membrane. Proteins are assayed by the Lowry method (Sigma).

Example 2

Demonstration of the Association of the LVPs with Human Immunoglobulins

Various fractions containing LVPs harvested from plasma from three patients infected with HCV and prepared according to the protocol of Example 1 were analyzed by polyacrylamide gel electrophoresis (PAGE) in the presence of SDS (Sodium Dodécyl Sulphate) (SDS-PAGE) (Laemmli, Nature (1970), 227: 680–685). The presence of immunoglobulins (Ig) in these fractions was demonstrated by the Western blot technique (Towbin et al., PNAS, (1979) 76: 4350–4354) using goat serum anti-human immunoglobulins coupled to peroxidase (Jackson ImmunoResearch laboratories, France). The results show that the human immunoglobulins are still detected in the fractions containing LVPs, in a different quantity depending on the patients.

The quantity of the HCV genome in these fractions containing LVPs was measured by quantification of the HCV RNA by RT-PCR (RT=reverse transcriptase; PCR= polymerase chain reaction) and detection of fluorescence in real time (LIGHTCYCLER™, ROCHE) (Wittwer et al., Biotechniques (1997), 22: 176–181). The results show that the HCV RNA is always associated with the fractions containing LVPs, in a different quantity depending on the patients.

The LVPs associated with the Ig's (LVP/Ig+) were furthermore purified using protein A coupled to beads of the MAGmol Protein A MicroBeads type (Miltenyi Biotec, France) after passage through MS+ Separation Columns (Miltenyi Biotec, France) or using Protein A-Sepharose CL-4B (Pharmacia Biotech, France). In this case, all or most of the HCV RNA copurifies with the Ig's, as illustrated in the tables which follow. Consequently, from a fraction rich in LVPs, the samples used for the infections may be purified via their Ig's so as to preferably use the LVP/Ig+/RNA+.

| Patient No. 1 | | |
| --- | --- | --- |
| | d* <1.0063 | d* 1.063 <d> 1.0063 |
| Presence of Ig | +++ | +++ |
| Quantification of RNA (for 0.2 ml of LVPs) | 27300 copies | 33600 copies |
| Quantification of RNA copurified with Ig | 23625 copies (86.5%) | 31875 copies (94.8%) | d* means the density of the LPVs in g/ml.

| Patient No. 2 | | |
| --- | --- | --- |
| | d* <1.0063 | d* 1.063 <d> 1.0063 |
| Presence of Ig | +++ | +/− |
| Quantification of RNA (for 0.2 ml of LVPs) | 32400 copies | 235800 copies |
| Quantification of RNA copurified with Ig | 21300 copies (65.7%) | 21300 copies (9%) | d* means the density of the LPVs in g/ml.

| Patient No. 3 | | |
| --- | --- | --- |
| | d* <1.0063 | d* 1.025 <d> 1.0055 |
| Presence of Ig | +++ | + |
| Quantification of RNA (for 0.2 ml of LVPs) | 197100 copies | 45900 copies |
| Quantification of RNA copurified with Ig | 142500 copies (72.3%) | 26100 copies (56.8%) | d* means the density of the LPVs in g/ml.

These results show that when immunoglobulins are present in the fractions containing LVPs, the viral RNAs are predominantly found in the fractions of LVPs associated with human immunoglobulins.

Example 3

Internalization of the LVPs by Cell Targeting

During the initial step of viral infection in vitro with the HCV virus purified according to Example 2, the use of an antibody directed against a cell receptor makes it possible to increase the efficiency of the targeting and of the internalization of the LVPs into a given cell line.

The LVPs associated with the Ig's (LVP/Ig+) were purified from a fraction having a density of between 1.025 and 1.055 g/ml using protein A coupled to beads of the MAGmol Protein A MicroBeads type (Miltenyi Biotec, France) as described in Example 2.

The human hepatocarcinoma line HepG2 cultured in DMEM-10% FCS medium was used for the study of the internalization of the purified LVP/Ig+ in the presence of an anti-LDL receptor antibody. The results were obtained according to the following protocol:

The HepG cells were inoculated at 45,000 cells/well on a 96-well plate, so as to obtain after 24 hours of incubation at 37° C.—5% $CO_2$, a confluence of about 70%.

Three washes in 1×PBS buffer were carried out and then the LVP/Ig+ fraction (that is $0.25 \times 10^6$ copies of HCV RNA) was added to each well in the presence of an increasing quantity of anti-LDL receptor antibody: that is 0, 1, 5, 10 and 20 µg/ml. Four wells were prepared per assay. The incubation was carried out at +37° C. for 3 hours.

The cells were washed 3 times using 1×PBS/0.2% BSA which is cold, and then treated with 10 mM suramine for 1 hour on an ice bed. After three new washes in 1×PBS, the cells were lysed with 350 µl of lysis buffer from the Rneasy kit (Qiagen). The RNAs were then purified using this same kit and analyzed by quantitative RT-PCR (LightCycler™).

The results obtained are indicated in FIG. 1. The results show that the higher the quantity of anti-LDL receptor antibody, the higher the quantity of LVP/Ig+ internalized (determined by quantification of the viral RNA). This can be explained by the formation of an LVP/Ig+—protein A/magnetic bead—anti-LDL receptor antibody complex which is produced by virtue of the presence of free protein A not coupled to the LVPs on the magnetic beads. This hypothesis is verified in the experiment described below.

The LVPs associated with the Ig's (LVP/Ig+) were purified from a fraction having a density of less than 1.006 g/ml using protein A coupled to beads of the MAGmol Protein A MicroBeads type (Miltenyi Biotec, France) as described in Example 2.

The HepG2 cells were inoculated at 50,000 cells/well (96-well plate), so as to obtain after 24 hours of incubation at 37° C.—5% $CO_2$, a confluence of about 80%. The results were obtained with the protocol described above, except that the LVP/Ig+ fraction (that is $0.4 \times 10^6$ copies of HCV RNA) was added for each assay with various conditions:

in the presence of 50 µg of human immunoglobulins, in the presence of 50 µg of human immunoglobulins and of 10 µg/ml of anti-LDL receptor antibody, in the presence of 10 µg/ml of anti-LDL receptor antibody, a preincubation of the LVP/Ig+ with the human immunoglobulins having been carried out for 1 hour at room temperature.

The results obtained are indicated in FIG. 2. These results confirm the specificity of the cellular targeting, in the sense that the incubation of the LVPs with immunoglobulins not specific for the receptor block the facilitation of the internalization by the anti-LDL receptor antibodies.

What is claimed is:

1. Complex consisting of lipo-viro particles (LVPs) associated with human immunoglobulins having a density of less than 1.063 g/ml.

2. Complex according to claim 1, having a density of between 1.0063 and 1.063 g/ml.

3. Method for preparing a complex consisting of lipo-viro particles (LVPs) associated with human immunoglobulins and having a density of less than 1.063 g/ml, preferably of between 1.0063 and 1.063 g/ml, according to which:

a plasma or serum sample from a patient infected with HCV is made available, the LVPs are separated from the sample by centrifugation according to their density, and the LVPs associated with human immunoglobulins are separated using protein A, anti-human immunoglobulins or any other molecule that binds human immunoglobulins.

4. Method according to claim 3, in which the protein A, the anti-human immunoglobulins or other molecule capable of binding human immunoglobulins are coupled to a support, such as beads or sepharose.

5. Method for the in vitro culture of the HCV virus, according to which a complex consisting of LVPs associated with human immunoglobulins according to claim 1, and permissive cells which contain at their surface at least one type of receptor for the Fc fragment of the immunoglobulins or permissive cells expressing a least one receptor for a molecule that binds the immunoglobulins are brought into contact, in a culture medium and under appropriate conditions, the permissive cells allowing the propagation and the replication of the HCV virus in vitro.

6. Method according to claim 5, according to which the permissive cells are chosen from the group consisting of mononuclear cells such as stem cells derived from the bone marrow, monoblasts, promonocytes, monocytes and macrophages, macrophage precursor cells, B lymphocytes, NK cells, the human or animal primary hepatocytes, the cells of the group of human or animal hepatocarcinoma cell lines, the Kuppfer cells, dendritic cells, epithelial cells, vascular endothelium cells, mastocytes, Langerhans' cells; syncytiotrophoblasts, eosinophilic, basophilic and neutrophilic polynuclear cells, platelets, erythrocytes and their precursors.

7. Method according to claim 6, in which the macrophages are preferably chosen from the group which consists of histiocytes, alveolar macrophages, macrophages of the spleen and of the lymphoid tissue, Kuppfer cells, osteoclasts, type A synovial cells, tissue macrophages and precursor cells from which these cells are derived.

8. Method according to claim 6, in which the permissive cells are primary or animal hepatocytes, the cells of the group of human or animal hepatocarcinoma cell lines or the Kuppfer cells which possess at least one type of receptor for the Fc fragment of the immunoglobulins and/or at least one receptor for lipoproteins such as the LDL receptor and the LSR receptor.

9. Method according to claim 5, in which the culture medium is the RPMI 1640 medium supplemented with 1% penicillin, 1% streptomycin, 2 mM glutamine, 10% FCS, and optionally further comprising 50 µM beta-mercaptoethanol.

10. Method according to claim 6, according to which the presence of the HCV virus in the permissive cells is detected by RT-PCR and/or by an immunological technique, such as by indirect immunofluorescence, in particular using an antibody specific for the said virus and/or by flow cytometry.

11. Method for preparing a composition for the detection, in a sample, of antibodies directed against the HCV virus which comprises at least a partial or complete purification of the HCV viral particles or of the polypeptides obtained from a method of culture according to claim 5.

12. Method according to claim 11, in which the said viral particles or the said polypeptides are attached to a solid support.

13. Method for producing antibodies or fragments of antibodies directed against the HCV virus, according to which an animal is immunized with a complex according to claim 1, or with at least one fraction of the said complex.

14. Method for the in vitro culture of the HCV virus according to which a complex consisting of LVPs associated with human immunoglobulins (LVP/Ig) as defined in claim 1 is made available, the complex is brought into contact with protein A for the production of an LVP/Ig/protein A complex, the LVP/Ig/protein A complex is brought into contact with at least one antibody specific for at least one cell receptor for the production of an LVP/Ig/protein A/antibody complex and the LVP/Ig/protein A/antibody complex and permissive cells which contain or express at their surface at least one cell receptor that binds the antibody are brought into contact, in a culture medium and under appropriate conditions; the permissive cells allowing the propagation and the replication of the HCV virus in vitro.

15. Method according to claim 14, in which the protein A is coupled to a support, such as beads or sepharose.

16. Method according to claim 14, in which the antibody is antibody specific for at least one of the receptors for the LDLs and the permissive cells contain or express at their surface at least one receptor for the LDLs.

17. Method according to claim 16, in which the permissive cells are chosen from human or animal primary hepatocytes and the cells of the group of human or animal hepatocarcinoma cell lines, such as the cells of the human heptacarcinoma line HepG2.

18. Method according to claim 14, in which the culture medium is the DMEM medium supplemented with 10% FCS.

19. Method according to claim 14, according to which the presence of the HCV virus in the permissive cells is detected by RT-PCR and/or by immunological technique, such as by indirect immunofluorescence, in particular using an antibody specific for the said virus and/or by flow cytometry.

20. Method for preparing a composition for the detection, in a sample, of antibodies directed against the HCV virus which comprises at least a partial or complete purification of the HCV viral particles or of the polypeptides obtained from a method of culture according to claim 14.

21. Method according to claim 20, in which the said viral particles or the said polypeptides are attached to a solid support.

22. Method for charging in vitro antigen presenting cells (APCs), according to which a complex consisting of LVPs associated with human immunoglobulins (LVP/Ig) as defined in claim 1 is made available, the said complex is brought into contact with protein A for the production of the LVP/Ig/protein A complex, the said LVP/Ig/protein A complex is brought into contact with at least one antibody specific for at least one cell receptor of the antigen presenting cells (APCs) collected from a human being or an animal for the production of an LVP/Ig/protein A/antibody complex and the said LVP/Ig/protein A/specific antibody complex is brought into contact with the said antigen presenting cells.

23. Method according to claim 22, in which the antigen presenting cells are dendritic cells and the antibody is an antibody specific for at least one cell receptor of the dendritic cells which is chosen from the "scavenger" receptors A and B, the mannose receptor and the "Toll Like Receptors" (TLRs).

24. Antigen presenting cells which can be obtained according to the method as defined in claim 22.

25. Therapeutic composition intended to induce a humoral and cellular response in a human being or an animal comprising a therapeutic agent which consists of antigen presenting cells charged according to claim 24.

26. Method for the production of antibodies or fragments of antibodies directed against the HCV virus, according to which an animal is immunized with an LVP/Ig/protein A/antibody complex which can be obtained by a method according to which, a complex consisting of LVPs associated with human immunoglobulins (LVP/Ig) as defined in claim 1 is made available, the said complex is brought into contact with protein A for the production of an LVP/Ig/protein A complex, the said LVP/Ig/protein A complex is brought into contact with at least one antibody specific for at least one cell receptor of antigen presenting cells (APCs) for the production of an LVP/Ig/protein A/antibody complex.

27. Method according to claim 26, in which the antigen presenting cells are dendritic cells and the antibody is an antibody specific for at least one cell receptor of the dendritic cells chosen from the "scavenger" receptors A and B, the mannose receptor and the "Toll Like Receptors" (TLRs).

* * * * *